United States Patent
Tidmarsh et al.

(10) Patent No.: US 6,989,140 B2
(45) Date of Patent: Jan. 24, 2006

(54) METHODS FOR CANCER IMAGING

(75) Inventors: George Tidmarsh, Portola Valley, CA (US); Mark Matteucci, Portola Valley, CA (US)

(73) Assignee: Threshold Pharmaceuticals, Inc., Burlingame, CA (US)

( * ) Notice: Subject to any disclaimer, the term of this patent is extended or adjusted under 35 U.S.C. 154(b) by 131 days.

(21) Appl. No.: 10/327,226

(22) Filed: Dec. 20, 2002

(65) Prior Publication Data

US 2003/0152518 A1 Aug. 14, 2003

Related U.S. Application Data

(60) Provisional application No. 60/342,313, filed on Dec. 21, 2001.

(51) Int. Cl.
*A61K 49/00* (2006.01)

(52) U.S. Cl. .................. 424/9.1; 424/1.11; 424/1.65; 424/1.73; 127/30

(58) Field of Classification Search ............ 424/1.11, 424/1.65, 1.73, 9.1, 9.2, 9.3, 9.4, 9.5, 9.6, 424/9.7, 9.8; 127/30, 36; 544/224

See application file for complete search history.

(56) References Cited

U.S. PATENT DOCUMENTS

| | | | |
|---|---|---|---|
| 4,716,225 A | 12/1987 | Ledley et al. | |
| 5,057,301 A | 10/1991 | Wilbur et al. | |
| 5,131,398 A | 7/1992 | Alfano et al. | |
| 5,261,410 A | 11/1993 | Alfano et al. | |
| 5,451,463 A | 9/1995 | Nelson et al. | |
| 5,512,667 A | 4/1996 | Reed et al. | |
| 5,585,422 A | 12/1996 | Falk et al. | |
| 6,031,091 A | 2/2000 | Arnold, Jr. et al. | |
| 6,083,487 A | 7/2000 | Biel | |
| 6,091,985 A | 7/2000 | Alfano et al. | |
| 6,099,822 A | 8/2000 | Ozker et al. | |
| 6,207,136 B1 | 5/2001 | Matsuoka | |
| 6,226,352 B1 | 5/2001 | Salb | |
| 6,256,530 B1 | 7/2001 | Wolfe | |
| 6,284,223 B1 | 9/2001 | Luiken | |
| 6,489,302 B1 | 12/2002 | Wiessler et al. | |

FOREIGN PATENT DOCUMENTS

| | | |
|---|---|---|
| EP | 0 413 145 A1 | 2/1991 |
| WO | WO 93/13403 A1 | 7/1993 |
| WO | WO 96/10363 A1 | 4/1996 |
| WO | WO 99/20316 A1 | 4/1999 |

OTHER PUBLICATIONS

Ball, S.W. et al. (2002). "A fluorescent compound for glucose uptake measurements in isolated rat cardiomyocytes," Can. J. Physiol. Pharmacol 80:205-209.

Leira, F. et al. (2002). "Fluorescent microplate cell assay to measure uptake and metabolism of glucose in normal human lung fibroblasts," Toxicology in Vitro 16:267-273.

Som, P. et al. (1980). "A Fluorinated Glucose Analog, 2-fluoro-2-deoxy-D-glucose (F-18): Nontoxic Tracer for Rapid Tumor Detection," J. Nucl. Med 21:670-675.

Yamada, K. et al. (2000). "Measurement of Glucose Uptake and Intracellular Calcium Concentration in Single, Living Pancreatic beta-Cells," The Journal of Biological Chemistry 275:22278-22283.

Yoshioka, K. et al. (1996). "A Novel fluorescent derivative of glucose applicable to the assessment of glucose uptake activity of *Escherichia coli*," Biochemica et Biophysica Acta 1289:5-9.

*Primary Examiner*—Dameron L. Jones
(74) *Attorney, Agent, or Firm*—Kevin R. Kaster; Photon Rao; William B. Kezer

(57) ABSTRACT

Methods are provided for cancer and pre-cancer detection by increased uptake of fluorophore glucose or deoxyglucose conjugates in cancerous and pre-cancerous cells relative to normal cells.

17 Claims, 4 Drawing Sheets

METHODS FOR CANCER IMAGING

CROSS-REFERENCES TO RELATED APPLICATIONS

This application claims priority to provisional U.S. patent application Ser. No. 60/342,313, filed 21 Dec. 2001, which is incorporated herein by reference in its entirety.

BACKGROUND OF THE INVENTION

The term "cancer" generally refers to one of a group of more than 100 diseases that are caused by the uncontrolled growth and spread of abnormal cells and can take the form of solid tumors, lymphomas and non-solid cancers such as leukemia. Unlike normal cells, which reproduce until maturation is attained and then only reproduce as necessary to replace wounded cells, cancer cells grow and divide endlessly without differentiating to mature, functional cells, crowding out nearby cells and eventually spreading to other parts of the body.

The most common sites in which cancer develops include the skin, lungs, female breasts, prostate, colon, rectum, bladder, uterus, blood-forming tissues, and lymphatic system. Cancer cells that have developed at one of these sites will grow rapidly into a malignant tumor, invading and destroying nearby tissues. Malignant cancer tumors will eventually metastasize, or spread to other parts of the body, unless their progression is stopped.

Cancers are easier to treat and cure if they are discovered and treated prior to metastasis. The survival of a patient with cancer is generally influenced by the stage at which the cancer is diagnosed. The stage, generally categorized as 1–4, is determined by the extent of disease, with stage 1 cancers being those that are small and not invading the surrounding tissues, while stage 4 cancers have established tumors in tissues other than the organ in which the cancer arose. Once cancer cells metastasize by leaving a tumor, they will travel through the bloodstream or lymphatic system to other parts of the body, where the cells begin multiplying and developing into new tumors. This sort of tumor progression makes cancer dangerously fatal. Although there have been great improvements in diagnosis, general patient care, surgical techniques, and local and systemic adjuvant therapies, most deaths from cancer are still due to metastases that are either resistant to conventional therapies or are undetected by current diagnostic methods.

The majority of diagnostic methods depend on microscopic observation of tissue biopsies. Many biopsy methods are invasive and require surgical removal of tissue for analysis.

Other useful methods for detecting cancer tissue in an animal include the use of positron emission tomography (PET scan). This method takes advantage of the increased uptake and retention by malignant cells of glucose and uses an $^{18}F$-labeled glucose derivative (FDG, $^{18}F$-2-fluoro-2-deoxyglucose). This glucose derivative, lacking a hydroxy group at the 2-position, cannot be further metabolized by the cells and is simply accumulated in the cells. This method of detection reveals live, growing tumor cells and therefore has advantages over anatomic detection methods which show abnormal structures but are insensitive to the viability of these abnormal tissues. While PET scanning is quite useful to image the entire patient for cancer, it requires expensive and cumbersome equipment for detection and construction of the positron used for the image. Accordingly, PET scanning cannot be used for the detection of cancer in many clinical settings, such as in the physician's office during the time of physical examination or in the operating room at the time of surgery.

Detection of a skin cancer such as melanoma has typically been through physical examination of the skin followed by biopsy of selected lesions suspected to be cancerous. Drawbacks to this procedure reside in the experience of the examiner, and errors in diagnosis can be life threatening. In instances where cancers are missed and then spread beyond the original site of disease, mortality can increase. Conversely, some skin lesions are biopsied which are not cancerous, and the patients are thus subjected to unnecessary harm. In some cases, biopsy samples are taken from the face, leading to cosmetic debility.

For those instances in which a patient has been diagnosed with cancer, the physician generally determines if the cancer can be removed, or resected, by surgery. Patients who have cancer that has not spread beyond a local area, stage 1 or 2, frequently may be cured by completely resecting the tumor. Prior to the surgery, various images of the tumor are obtained such as X-rays, CT scans, MRI scans or PET images. These tests provide guidance for surgery, but at the time of surgery, these images cannot be generated in real time to guide the surgeon to the tumor. As a result, the surgeon must use the unaided senses of sight and feel to determine the location and extent of the tumor.

In some instances, the surgeon will obtain biopsy samples in the area of the resected tumor prior to completing the operation. These samples are examined under the microscope to determine if all of the cancer has been removed. However, this procedure is often not conducted, as it requires a highly trained pathologist to be present at the surgery and to rapidly analyze the tissue sample while the patient remains on the operating table. If this analysis is used and the cancer remains in the patient, the surgeon continues with unaided senses to try to resect any residual tumor. Unfortunately, despite such efforts, residual tumor will be left inside the patient about 15–25% of the time. Studies have shown that these patients are at greater risk of dying of the cancer than those that have the tumor completely resected. Because of this, these patients require further, often debilitating, costly therapy in an attempt to arrest and treat the cancer left in the patient at the time of surgery.

Screening for tumors in the colon or lung is currently carried out by endoscopy using white light and a video capture screen. Due to the native fluorescence of lung tumor tissue, a special adapter for the endoscope is used to detect this autofluorescence, thereby enabling the observer to detect smaller tumors at an earlier time. However, even with this enhanced method of screening, smaller tumors and cancer cells can go undetected.

To image cancer tissue at the time of screening or at the time of surgery, attempts have been made to use radioactive isotopes or photosensitizers linked to targeting entities such as monoclonal antibodies. These detection methods are limited in that they cannot be used in the general physician's practice for screening large numbers of patients nor can they be used at the time of surgery to locate the residual tumor. Other detection methods are described in U.S. Pat. Nos. 6,256,530, 6,091,985, 6,083,487; EP patent publication No. 0588994 A1; and PCT patent publication Nos. WO 96/10363 and WO 93/13403.

What is needed are methods and reagents for detecting cancer tissue, including tumors, non-solid cancers, and cancer cells, that are convenient, without the drawbacks of the methods and reagents noted above, and that are widely applicable in a variety of clinical settings, including surgery.

The present invention provides such methods, as well as compounds and compositions useful in the methods.

SUMMARY OF THE INVENTION

The present invention provides compounds, compositions and methods for detecting and imaging cancerous and pre-cancerous cells and tissues.

In one aspect, the present invention provides methods for detecting or imaging cancer in a subject, comprising:

(a) administering to the subject an effective amount of a fluorophore glucose or deoxyglucose conjugate; and (b) detecting or imaging cells that take up the fluorophore conjugate or derivative to determine cancerous or pre-cancerous cells or tissue are present in the subject.

In one embodiment, the fluorophore conjugate has the formula:

wherein Fl is a fluorophore; L is a bond or a linking group; and Glc is glucose, deoxyglucose, or a glucose or deoxyglucose derivative. Preferred glucose derivatives are D-(+)-deoxyglucose, D-(+)-glucosamine and N-acetyl D-glucosamine. The above method can be carried out in combination with a surgical procedure, such as a cancer resection. The method of detecting can be carried out endoscopically for example, or visually, for example as part of a skin examination for melanoma screening.

Additionally, this method finds broad applicability to the detection of a number of cancers, due in large part to its ability to detect and/or image cancer at the cellular level from such cancers as lung cancer, breast cancer, prostate cancer, colon cancer, cervical cancer, esophageal cancer, bladder cancer, head and neck cancer, and melanoma.

In some embodiments, additional steps can be employed, such as a preliminary step of reducing glucose ingestion in a subject prior to administering the fluorophore glucose or deoxyglucose conjugate. Typically, this can be accomplished by withholding carbohydrate consumption for a period of up to 18 hours prior to administration of the conjugate. In other embodiments, carbohydrate consumption is stopped for a period of 8 to 48 hours prior to administration of the conjugate.

In a related aspect, the present invention provides methods for detecting or imaging pre-cancerous cells in a subject, comprising:

(a) administering to the subject an effective amount of a fluorophore glucose or deoxyglucose conjugate; and (b) detecting or imaging pre-cancerous cells that take up the fluorophore glucose or deoxyglucose conjugate to determine if pre-cancerous cells are present in the subject.

In another related aspect, the present invention provides a method for cancer or pre-cancer detection during an operative or endoscopic procedure, the method comprising:

(a) administering to a patient subject to such a procedure, an effective amount of a fluorophore glucose or deoxyglucose conjugate, the conjugate having a rate of uptake in cancerous or pre-cancerous cells that is at least two times greater than the rate of uptake in normal cells;

(b) conducting the procedure within 48 hours of administering the conjugate; and (c) scanning the patient with a detection means for detecting the localization of the fluorophore conjugate in the cancerous or pre-cancerous cells.

In preferred embodiments of this aspect, the procedure is conducted within about 24 hours of administering the conjugate. More preferably, the method further comprises treating sites of conjugate accretion by external beam radiation, laser therapy or surgical removal.

In yet another aspect, the present invention provides a fluorophore glucose or deoxyglucose conjugate having the formula:

wherein Fl is a fluorophore having an emission wavelength of from about 400 nm to about 1200 nm; L is a bond or a linking group; and Glc is glucose or deoxyglucose or a glucose or deoxyglucose derivative, with the proviso that the conjugate is other than 2-(N-(7-nitrobenz-2-oxa-1,3-diazol-4-yl)amino)-2-deoxyglucose (2-NBDG).

The present invention further provides kits comprising a container with a sterile preparation for human use of a fluorophore glucose or deoxyglucose conjugate and a pharmaceutically acceptable carrier.

DETAILED DESCRIPTION OF THE INVENTION

Figure 1:
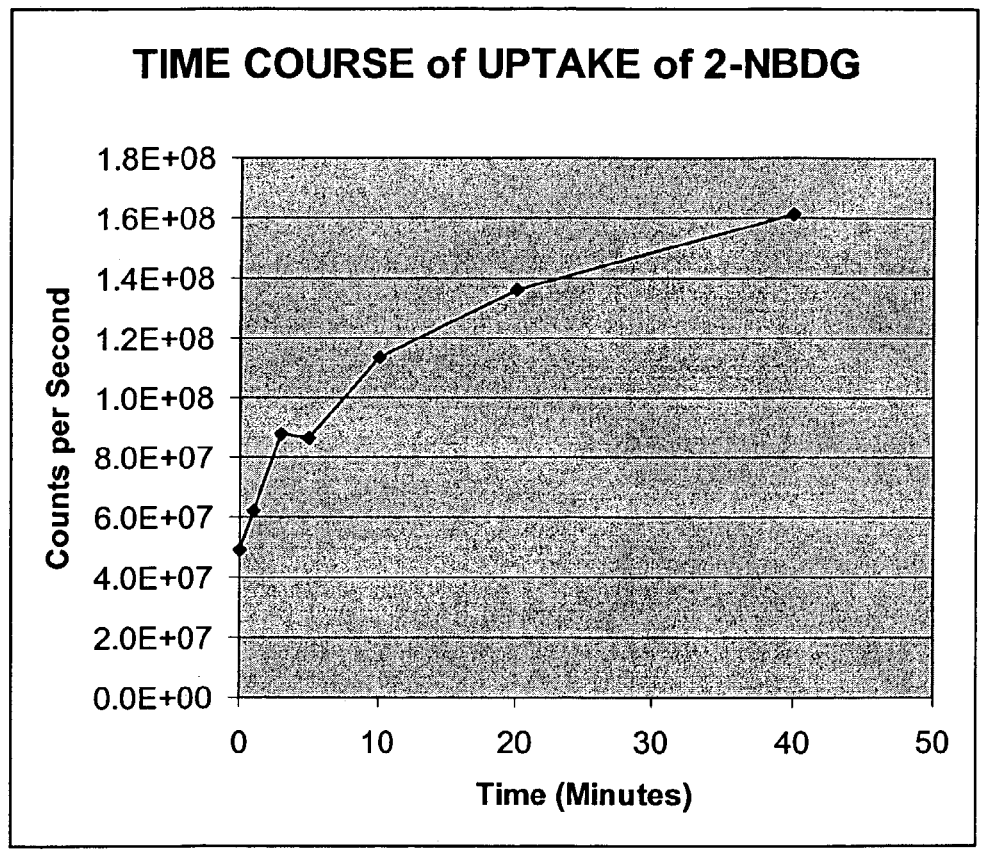
FIG. 1 is a graph illustrating the results of a time-course uptake of 2-(N-(7-nitrobenz-2-oxa-1,3-diazol-4-yl)amino)-2-deoxyglucose in Raji lymphoma cells.

The present invention arises in part from the discovery that cancerous and pre-cancerous cells exhibit an enhanced rate of uptake of glucose fluorophore (fluorescent) conjugates.

The present invention makes possible the imaging of tumor tissue during screening visits to a doctor and at the time of surgery by using fluorophore glucose or deoxyglucose conjugates. Some of these conjugates are derived by chemically modifying 2-deoxyglucose or an analog thereof, which is taken into and accumulated in cancerous cells and pre-cancerous cells (e.g., dysplastic cells) preferentially, compared to normal cells. After allowing the fluorophore glucose conjugate to accumulate in the cancerous cells, an examination can be made of the cancer or of the patient with either a camera or other device to view or capture the fluorescence. This method allows cancerous tissue to be detected more specifically and with greater sensitivity than existing methods of detection.

In one embodiment of the present invention, the method is used by a surgeon to visualize, in real time, tumor tissue during a surgical resection and to assess the margin of the tumor, allowing a more complete resection of the tumor tissue and a better outcome for the patient.

Additionally, administration of the fluorophore conjugate to a human prior to examination can be carried out to determine if the human subject has cancerous or pre-cancerous tissue in any observed organ. For example, an individual who is at high risk for developing melanoma because of skin type and family history can be administered a fluorophore conjugate prior to examination. After accumulation of the conjugate in any tumor tissue, visualization of the tumor can be made with appropriate equipment. In addition to standard methods of examination, a diagnosis can be made by determining if any of the pigmented lesions on the skin are cancerous and must be removed. The present invention eliminates many errors of diagnosis that can lead to either the unneeded removal of benign tissue or the mistake of leaving a cancer on the skin, allowing it to spread throughout the body.

The methods of the present invention are useful in the course of surgery, visual examinations, endoscopic examinations, and the like. Typically, the methods will involve contacting sites on a subject suspected of being cancerous sites with a suitable fluorophore conjugate, and visualizing the cells and tissues that have taken up the conjugate to determine in real time whether cancerous or pre-cancerous cells are present in the subject.

The methods described herein do not require the processing of images but instead can be carried out by the clinician or surgeon with the use of, e.g., an intraoperative probe, an intravascular probe, or an endoscope to scan areas of suspected cancerous cells or tissue and to correlate the level of fluorescence observed with the presence or absence of cancerous cells and to discriminate cancerous cells and tissue from non-cancerous cells and tissue more precisely. Using this method, the surgeon or clinician can more precisely define tumor borders for surgical resection or diagnostic evaluation. Additionally, drug delivery, laser therapy, radiation therapy, external beam therapy, and the like can be more specifically targeted to cancerous cells and tissues harboring them that have been identified by the methods described herein.

Methods of Detecting or Imaging Cancer

In view of the above, the present invention provides, in one aspect, methods for detecting or imaging cancerous cells or tissue in a subject, comprising:

(a) administering to the subject an effective amount of a fluorophore glucose or deoxyglucose conjugate; and (b) detecting or imaging cells that take up the fluorophore conjugate to determine if cancer is present in the subject.

The present methods find broad applicability in the detection of a number of cancers, due in large part to their utility in detecting cancer at the cellular level from all types of cancers, including but not limited to such cancers as lung cancer, breast cancer, prostate cancer, colon cancer, cervical cancer, esophageal cancer, bladder cancer, head and neck cancer, melanoma, low grade non-Hodgkin's Lymphoma, intermediate grade non-Hodgkin's Lymphoma, follicular lymphoma, large cell lymphoma, B-cell lymphoma, T-cell lymphoma, Mantle cell lymphoma, Burkitt's lymphoma, NK cell lymphoma, and acute lymphoblastic lymphoma.

The fluorophore conjugate used in this aspect of the invention is preferably one having the formula:

Fl-L-Glc     (I)

wherein Fl is a fluorophore; L is a bond or a linking group; and Glc is glucose or deoxyglucose or a glucose or deoxyglucose derivative.

Fluorophores

A variety of fluorophores are useful in this aspect of the invention, including certain commercially available fluorophores such as fluorescein derivatives (e.g., fluorescein isothiocyanate), rhodamine derivatives and derivatives of the chelates of rare earth metals such as europium.

Selection of a suitable fluorophore generally involves consideration of certain physical and chemical properties such as fluorescence intensity, fluorescence lifetime, excitation and emission wavelength maxima, polarization, and non-specific binding behavior.

(a) Fluorescence Intensity

Fluorescence intensity is the intensity of the fluorescence produced upon excitation of the fluorophore with light (such as from a laser source) and can be dependent on the nature of the solvent used for the fluorescence measurement. Use of an aqueous solvent system, such as a biological buffer, is convenient and preferred for certain applications, such as immunoassays.

(b) Excitation and Emission Wavelengths

The excitation and emission wavelengths are, respectively, the wavelengths of light required to produce fluorescence and the wavelengths of light at which fluorescence emission occurs. Fluorescence emission occurs at a longer wavelength than the excitation wavelength. Ultraviolet, visible, and infrared light (typically wavelengths in the range of about 200 nanometers to about 1000 nanometers) are considered to be wavelengths that are potentially useful in exciting a fluorophore molecule and thereby producing detectable fluorescence. Due to the abundance of naturally occurring substances which fluoresce upon excitation at relatively short wavelengths (in the range of about 200 nm to about 500 nm), improved sensitivity of detection can be achieved by using a conjugate having a fluorophore which, in the conjugate, fluoresces upon excitation by light of wavelength greater than about 500 nm, preferably in the spectral range of about 500 nm to about 900 nm.

Those of skill in the art will be able to select a conjugate of the invention having the desired properties for the particular application of interest to the practitioner. There are a variety of fluorophores that can be selected to avoid or minimize the background signal from autofluorescence of the surrounding tissue or fluids or to enhance fluorescence from a fluorophore present in cancerous as opposed to surrounding benign tissue. Thus, as but one example, U.S. Pat. No. 5,131,398, to Alfano et al., describes diagnosis of cancerous cells by using a substantially monochromatic excitation light and two detection bands at ~340 and 440 nm. The patent reports that, when tissue is monochromatically excited at 300 nm, the resulting native fluorescence spectrum from 320 nm to 600 nm in cancerous tissue is substantially different from that of either benign or healthy tissue. The patent further disclosed that, by avoiding the use of fluorescent emissions between about 380 nm and 430 nm, the fluorescent effect from blood could be ignored. In addition, the patent reported that, at excitation wavelengths above 315 nm, the ratios of fluorescent-emission intensities are indistinguishable between cancerous and benign cells. The diverse fluorophore deoxyglucose conjugates of this invention allow the practitioner to select the conjugate best suited to detect cancer cells in the tissue or tissues of interest given such parameters.

(c) Fluorescence Lifetime and Fluorescence Decay Time

The lifetime of the fluorescence produced by the fluorophore may vary from less than one nanosecond to several milliseconds. Some organic dyes that exhibit fluorescence lifetimes in the range of 3 to 50 nanoseconds belong to the general class of aromatic compounds, exemplified by aromatic hydrocarbon derivatives such as perlene carboxylic acid and aromatic heterocyclic compounds such as phthalocyanines and naturally occurring porphyrins. These dyes have a characteristic fluorescence lifetime, that is, the time period following excitation during which they emit light and during which the fluorescence intensity decreases to about 37% (1/e) of its initial value in the absence of any deactivating factors. The measured fluorescence decay time is the time period during which the decrease to the 37% (1/e) level of fluorescence intensity is observed. The measured decay time of a particular compound may be solvent dependent. Under conditions which minimize deactivation, measured decay time may approach fluorescence lifetime.

(d) Fluorescence Polarization

When a fluorescent substance in solution is excited with polarized light, it emits partially polarized light as fluorescence. The degree of polarization of fluorescence can be measured and is related to the molecular volume of the fluorophore. Accordingly, generally preferred fluorophores are those which efficiently fluoresce upon excitation with light whose wavelength falls within the range of about 200 to about 1000 nanometers, preferably in the range of about 600 to 800 nanometers. Suitable fluorophores include those which absorb and/or emit at wavelengths which are distinguishable from the excitation and emission maxima of the other solution components (such as proteins present in a sample) to minimize background fluorescence. For those methods involving detection or imaging during surgery, fluorophores having excitation and/or emission wavelengths of at least about 500 nanometers are preferred. The use of such fluorophores reduces interference from the ambient fluorescence of other biological components. Preferred fluorophores also exhibit a high degree of fluorescence polarization, preferably greater than about 10% of the theoretical maximum value for an observable polarization.

Preferred fluorophore moieties include fluorescent dyes having (a) high fluorescence intensity; (b) sufficiently long excitation and emission wavelength maxima so that interference from natural fluorescence of either diseased or normal tissue is minimized; (c) sufficiently long measured fluorescence decay time to allow accurate measurement of emitted light over background fluorescence and scattering (at least about 2, preferably at least about 10 nanoseconds); and (d) high degree of fluorescence polarization. Additionally, in one embodiment of the invention, a fluorophore glucose, deoxyglucose or derivative conjugate that is transportable by the glucose transporter is provided and is preferred in some applications of the methods of the invention. In this embodiment, the preferred fluorophore has the additional quality of small size.

Preferred fluorophores include, for example, 5-(and 6) carboxynaphtofluorescein and Texas Red, as described in the examples below, especially for conjugation to the terminal primary amino group of a linker attached to glucosamine. Additionally, other preferred fluorophores are: (i) BODIPY 630/650, which can be conveniently coupled to primary amines using an active ester derivative that is available commercially (Molecular Probes, Inc., Catalog number, B-10003); (ii) BODIPY 650/665, which can be conveniently coupled to primary amines using an active ester derivative that is available commercially (Molecular Probes, Inc., Catalog number, B-10005); (iii) Dansyl, which can be conveniently coupled to primary amines using dansyl chloride that is commercially available (Aldrich Chemical); (iv) Rhodamine, which can be conveniently coupled to primary amines using an active ester derivative that is available commercially (Molecular Probes, Inc., Catalog number, R-6107); (v) 5-TAMRA, which can be conveniently coupled to primary amines using an active ester derivative that is available commercially (Molecular Probes, Inc., Catalog number, C-2211).

As noted, in one aspect of the present invention, preferred fluorophores include macrocyclic fluorescent dye compounds, especially compounds having aromatic π-electron systems. These dye compounds act as multidentate macrocyclic ligands to chelate a central complexing atom. Thus, these preferred fluorophore moieties may comprise a substantially planar multidentate macrocyclic ligand coordinated to a complexing central ion or atom. Preferred elements include aluminum, phosphorous, and the group IVB elements, e.g. silicon, germanium, and tin.

Other suitable fluorophores include coumarin dyes, nitrobenzoxazole dyes, cyanine dyes, dipyrromethaneboron dyes, xanthene dyes (including the benzo- and naphtho-xanthene dyes), phenoxazine dyes (as well as the benzo- and naphtho-phenoxazine dyes) and compounds from other classes of dyes well known to those of skill in the art. Other suitable fluorophores include the fluorophores in the following non-exclusive list: 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-FAM (5-Carboxyfluorescein); 5-HAT (Hydroxy Tryptamine); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Aequorin (Photoprotein); AutoFluorescent Protein-(Quantum Biotechnologies) see sgGFP, sgBFP; Alexa Fluor (various)™; Alizarin Complexon; Alizarin Red; Allophycocyanin (APC); AMC, AMCA-S; AMCA Aminomethylcoumarin); AMCA-X; Aminoactinomycin D; Aminocoumarin; Aminomethylcoumarin (AMCA); Anilin Blue 600; Anthrocyl stearate; APC (Allophycocyanin); APC-Cy7; APTRA-BTC=Ratio Dye, Zn2+; APTS; Astrazon Brilliant Red 4G, Orange R, Red 6B, and Yellow 7 GLL; Atabrine; ATTO-TAG™ CBQCA and FQ; Auramine; Aurophosphine; BAO 9 (Bisaminophenyloxadiazole); BCECF (high or low pH); Berberine Sulphate; Beta Lactamase; BFP blue shifted GFP; Blue Fluorescent Protein; blue shifted GFP (Y66H); BFP/GFP FRET; Bimane; Bisbenzamide; bis-BTC=Ratio Dye, Zn2+; Blancophor FFG and SV; BOBO™-1 and -3; Bodipy (various); BO-PRO™-1 and -3; Brilliant Sulphoflavin; BTC—Ratio Dye Ca2+; BTC-5N; Calcein; Calcein Blue; Calcium Crimson™; Calcium Green (various) and Orange; Calcofluor White; Carboxy-X-rhodamine (5-ROX); Cascade Blue™; Cascade Yellow; Catecholamine; CCF2 (GeneBlazer); CFDA; CFP—Cyan Fluorescent Protein; Cyan Fluorescent Protein; CFP/YFP FRET; Chlorophyll; Chromomycin A; CL-NERF (Ratio Dye, pH); CMFDA; Coelenterazine Dye (various); Coumarin Phalloidin; C-phycocyanine; Methylcoumarin; Methylcoumarin CTC; CTC Formazan; Cy2™ and various others; Cyan GFP; cyclic AMP Fluorosensor (FiCRhR); Dabcyl (various); Dansyl (various); DAPI; Dapoxyl (various); DCFDA; DCFH (Dichlorodihydrofluorescein Diacetate); DDAO; DHR (Dihydorhodamine 123); Di-4-ANEPPS; Di-8-ANEPPS; DiA (4-Di-16-ASP); Dichlorodihydrofluorescein Diacetate (DCFH); DiD—Lipophilic Tracer; DiD (DiIC18(5)); DIDS; Dihydorhodamine 123 (DHR); DiI (DiIC18(3)); Dinitrophenol; DiO (DiOC18(3)); DiR (various); DM-NERF (high pH); DNP; Dopamine; DsRed; DTAF; DY-630-NHS; DY-635-NHS; EBFP; Enhanced Blue Fluorescent Protein; Enhanced Cyan Fluorescent Protein;

Enhanced Green Fluorescent Protein; ELF; Eosin; Erythrosin; Erythrosin; Ethidium Bromide; Ethidium homodimer-1 (EthD-1); Euchrysin; EukoLight; Europium (III) chloride; EYFP; Enhanced Yellow Fluorescent Protein; Fast Blue; FDA; Feulgen (Pararosaniline); FIF (Formaldehyd Induced Fluorescence); Flazo Orange; Fluo-3; Fluo-4; Fluorescein (FITC); Fluorescein Diacetate; Fluoro-Emerald; Fluoro-Gold (Hydroxystilbamidine); Fluor-Ruby; FluorX; FM 1-43™; FM 4-46; Fura Red™ (various); Genacryl Brilliant Red B, Brilliant Yellow 10GF, Pink 3G, and Yellow 5GF; GeneBlazer (CCF2); GFP (various); Gloxalic Acid; Granular Blue; Haematoporphyrin; Hoechst 33258, 33342, and 34580; HPTS; Hydroxycoumarin; Hydroxystilbamidine (FluoroGold); Hydroxytryptamine; Indo-1 (various); Indodicarbocyanine (DiD); Indotricarbocyanine (DiR); Intrawhite Cf; JC-1; JO-JO-1; JO-PRO-1; LaserPro; Laurodan; LDS 751; Leucophor PAF, SF, and WS; Lissamine Rhodamine (various); Calcein/Ethidium homodimer; LOLO-1; LO-PRO-1; Lucifer Yellow; Lyso Tracker (various); LysoSensor (various); Mag Green; Magdala Red (Phloxin B); Mag-Fura Red; Mag-Fura-2; Mag-Fura-5; Mag-Indo-1; Magnesium Green and Orange; Malachite Green; Marina Blue; Maxilon Brilliant Flavin; Maxilon Brilliant Flavin; Merocyanin; Methoxycoumarin; Mitotracker Green, Orange, and Red; Mitramycin; Mono-bromobimane; Monobromobimane (mBBr-GSH); Monochlorobimane; MPS (Methyl Green Pyronine Stilbene); NBD; NBD Amine; Nile Red; Nitrobenzoxadidole; Noradrenaline; Nuclear Fast Red; Nuclear Yellow; Nylosan Brilliant lavin; Oregon Green™ (various); Pacific Blue; Pararosaniline (Feulgen); PBFI; PE-Cy5 and Cy7; PerCP; PE-TexasRed [Red 613]; Phloxin B (Magdala Red); Phorwite (various); Phosphine; PhotoResist; Phycoerythrin B and R; PKH26 and 67; PMIA; Pontochrome Blue Black; POPO-1 and -3; PO-PRO-1 and -3; Primuline; Procion Yellow; Propidium Iodid (PI); PYMPO; Pyrene; Pyronine; Pyronine B; Pyrozal Brilliant Flavin; QSY; Quinacrine Mustard; Red 613 [PE-TexasRed]; Resorufin; Rhodamine (various); Rose Bengal; R-phycocyanine; R-phycoerythrin (PE); red shifted GFP (various); Sapphire GFP; SBFI; Serotonin; Sevron Brilliant Red, Orange, and Yellow L; SuperGlo™GFP (various); SITS (various); SNAFL (various); SNARF; Sodium Green; SpectrumAqua, Green, Orange, and Red; SPQ (6-methoxy-N-(3-sulfopropyl)quinolinium); Stilbene; Sulphorhodamine B and G; SYTO (various); SYTOX Blue, Green, and Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5, S, and TCN; Thiolyte; Thiozole Orange; Tinopol CBS (Calcofluor White); TMR; TO-PRO-1, -3 and -5; TOTO-1 and -3; TriColor (PE-Cy5); TRITC; TetramethylRodamineIsoThioCyanate; True Blue; TruRed; Ultralite; Uranine B; Uvitex SFC; X-Rhodamine; XRITC; Xylene Orange; Y66F, H, and W; Yellow shifted Green Fluorescent Protein; Yellow Fluorescent Protein; YO-PRO-1 and -3; and; YOYO-1 and -3.

Linking Groups

The fluorophores used herein can be attached to the glucose or deoxyglucose or glucose or deoxyglucose derivative using any linkage chemistry that is compatible with the fluorophore and the glucose or deoxyglucose or glucose or deoxyglucose derivative portions of the conjugate.

In some embodiments, the fluorophore can be attached directly to glucose or deoxyglucose or a glucose or deoxyglucose derivative using, for example, a fluorophore isothiocyanate (e.g., fluorescein isothiocyanate) and a suitably protected glucose or glucose derivative (e.g., tetra O-acetyl-2-deoxy-2-aminoglucose) to form a desired conjugate. A number of protected glucose or deoxyglucose compounds or derivatives are commercially available or can be prepared according to well-established methods. In many instances, the glucose or deoxyglucose moiety having "n" hydroxy or amino groups, will have "n–1" protecting groups, thereby leaving one available reactive functional group as an attachment site for either the fluorophore or a linking group. Additionally, the unprotected functional group will be at a known location on the glucose, deoxyglucose or derivative thereof to prepare conjugates of a desired structure.

In certain embodiments, a linking group is used to attach the fluorophore to the glucose or deoxyglucose or glucose or deoxyglucose derivative covalently. In these embodiments, any commercially available bifunctional linking groups, preferably, heterobifunctional linking groups (see Pierce Catalog), can be used. Alternatively, one of skill in the art can construct a linking group having two or more reactive functional groups to attach the fluorophore and the glucose or deoxyglucose moiety (e.g., heterobifunctional or homobifunctional). In some embodiments, either a plurality of glucose or deoxyglucose moieties or a plurality of fluorophores or both are attached to a multifunctional linking group to provide a conjugate of the invention.

The terms "linker" and "linking group" refer to a moiety that is used to connect various portions of the conjugate to one another. Typically a linker or linking group has functional groups that are used to interact with and form covalent bonds with functional groups in the components (e.g., fluorophores and glucose or glucose derivatives) of the conjugates described and used herein. Examples of functional groups on the linking groups (prior to interaction with other components) include —$NH_2$, —$NHNH_2$, —$ONH_2$, —NHC=(O)$NHNH_2$, —OH, —$CO_2H$ or —SH. One of skill in the art will understand that each of these functional groups can form a covalent linkage to a suitable functional group on the glucose portion or the fluorophore portion of the conjugate during synthesis of the conjugate. For example, amino, hydroxy and hydrazino groups can each form a covalent bond with a reactive carboxyl group (e.g., a carboxylic acid chloride or activated ester such as an N-hydroxysuccinimide ester (NHS)). Other suitable bond forming groups are well-known in the literature and can be used to prepare conjugates of the present invention.

The linking group can include linear or acyclic portions, cyclic portions, aromatic rings or combinations thereof. More specifically, the linking group L will typically have from 3 to 100 main chain atoms other than hydrogen atoms, selected from C, N, O, S, P and Si, and will be cyclic, acyclic, aromatic or a combination thereof. Additionally, the linking groups will be sufficiently robust so that they are stable to reaction conditions used in conjugate assembly, e.g., the protection/deprotection chemistries used to prepare the conjugates of the invention. Illustrative linkers and synthetic chemistries are described in more detail below.

In addition to commercially available linking groups, U.S. Pat. Nos. 5,512,667; 5,451,463; and 5,141,813 describe other linking groups that can be used to prepare conjugates of the present invention. U.S. Pat. Nos. 5,696,251; 5,585,422; and 6,031,091 describe certain tetrafunctional linking groups that can be useful in preparing conjugates of the present invention, such as, for example, conjugates comprising two or more fluorophores. Functional groups or linkers useful in preparing conjugates of the present invention include primary and secondary nitrogen, primary and secondary OH, and —SH.

As discussed in the following section, a preferred deoxyglucose moiety for forming the conjugates of the present invention is D-glucosamine as the hydrochloride salt. This compound has an amino group that provides a chemical handle for conjugations. Fluorophores can be conjugated directly to this amino group via alkyl, amide, or sulfonamide linkages, for example. Alternatively, a linker or spacer can separate the fluorophore and the glucosamine. The glucosamine is then not sterically impacted by the fluorophore and is free to act like glucose in term of uptake via the glucose transport system and phosphorylation via the hexokinase enzymes. Optimal linkers are oligomers of ethylene glycol or straight alkyl chains. These linkers are attached to the glucosamine amine via either an alkyl or amide connection. The fluorophore is attached to the other end via an amide, sulfonamide, or ether connection. The optimum length of the linker is from 4 to 16 atoms. Illustrative synthetic schemes for forming such conjugates of the invention are shown below for several preferred linkers of the invention. The 5-(and 6) carboxynaphtofluorescein is shown as an example of a fluorophore (only one isomer shown in schemes), but any fluorophore as an N-hydroxysuccimide (NHS) ester can be used in these illustrative schemes to form a conjugate of the invention.

Synthesis of Carboxynaphtofluorescin-oligo-PEG Amidoglucosamine Conjugates

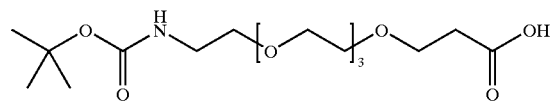

N-t-boc-amido-PEG4-acid,
product number 10220, Quantabiodesign Inc 1) 1 equivalent 1-(3 Dimethylamino)-3-ethylcarbodiimide HCl
2) 2 equivalents N Hydroxysuccinimde (NHS)
  solvent DMF

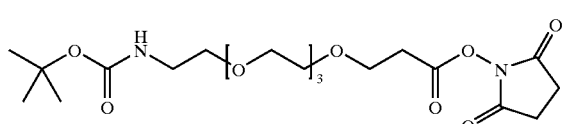

1) 1 equivalent

H₂N-glucosamine·HCl structure 2) 1 equivalent Triethyl amine
  solvent DMF

-continued

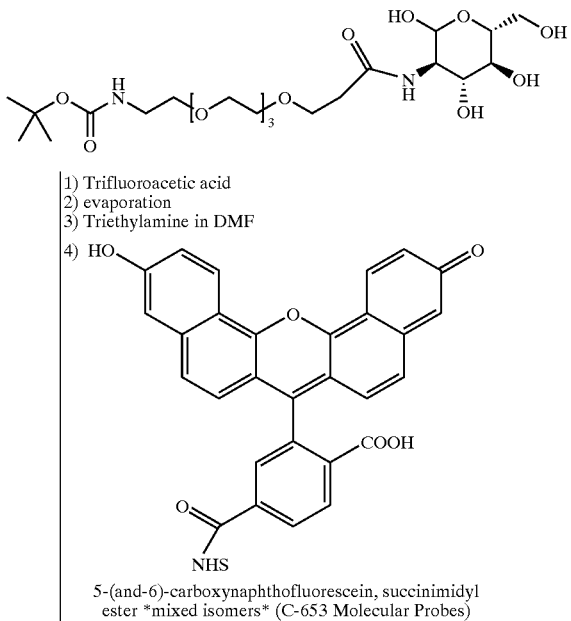

1) Trifluoroacetic acid
2) evaporation
3) Triethylamine in DMF
4)

5-(and-6)-carboxynaphthofluorescein, succinimidyl ester *mixed isomers* (C-653 Molecular Probes)

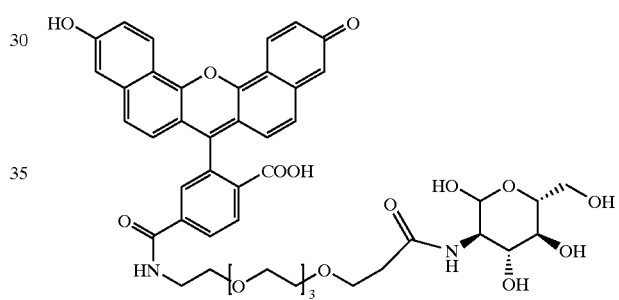

The length of the linker arm can be varied. For example, in the case of the amide connections, one can use the derivatives shown below in place of N-t-boc-amido-PEG4-acid, product number 10220, Quantabiodesign Inc.

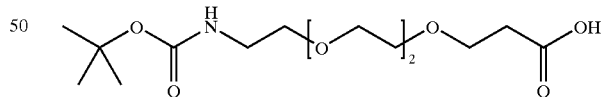

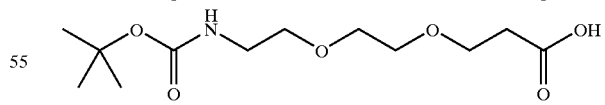

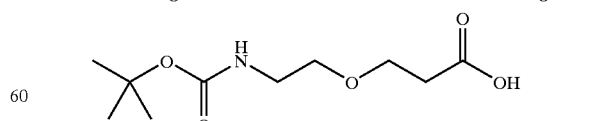

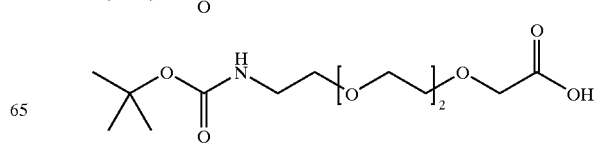

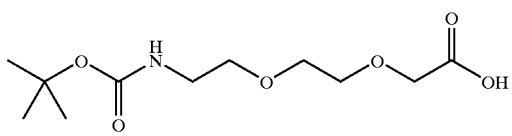

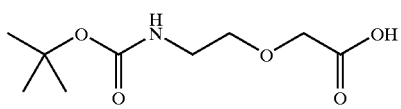

These t-boc protected amino acids can be derived from the corresponding amino acid and BOC-ON (19,337-2, Aldrich Chemical). The amino acids in turn can be obtained from published procedures in the chemical literature.

Synthesis of Carboxynaphtofluorescin-oligo-PEG-alkyl-glucosamine Conjugate

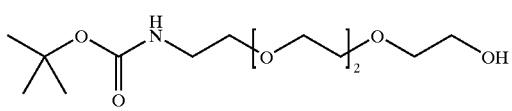

N-t-boc-amido-PEG4-alcohol,
product number 10250, Quantabiodesign Inc 1) 1 equivalent Dess-Martin periodinane

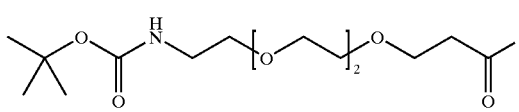

1) 3 equivalents

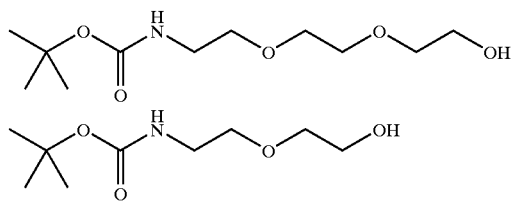

Ac = acetyl
Synthesis of protected glucosamine:
PCT application, IPN WO 99/20316
IPD 4/29/99, Kulkarni and Devous, p15
2) 3 equivalents sodium triacetoxy borohydride
solvent THF

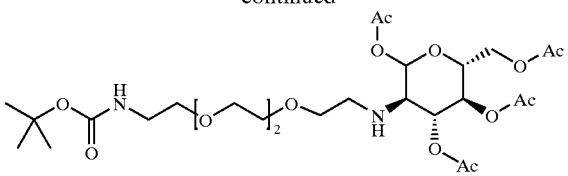

1) Sodium methoxide in methanol
2) Trifluoroacetic acid
2) evaporation
3) Triethylamine in DMF
4) 0.5 equivalent

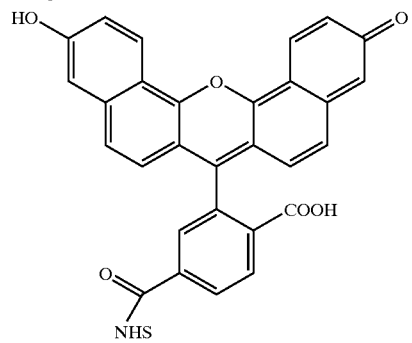

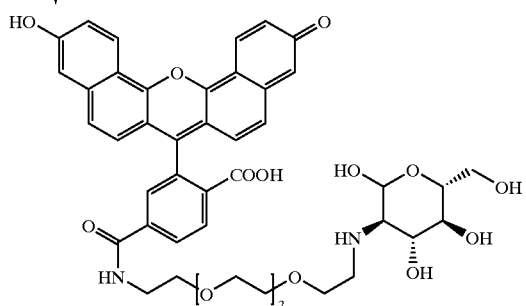

The length of the linker arm can be varied. For example, in the case of the alkyl connection, one can use the derivatives shown below in place of N-t-boc-amido-PEG4-alcohol, (product number 10250, Quantabiodesign Inc.).

These t-boc protected amino alcohols can be derived, for example, from the corresponding amino alcohols and BOC-ON (19,337-2, Aldrich Chemical). The amino alcohols in turn can be obtained from published procedures in the chemical literature.

Alternatively, the starting amino acids and alcohols for the conjugates can comprise all alkyl chains as shown below. The amino acids and alcohols are available commercially (Aldrich Chemical) and can be derivatized with BOC-ON (19,337-2, Aldrich Chemical) to produce the reagents shown below.

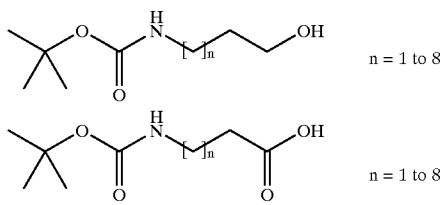

n = 1 to 8 n = 1 to 8

Glucose and Deoxyglucose and their Derivatives

The glucose, deoxyglucose or derivative components of the conjugates described herein are preferably D-(+)-deoxyglucose, D-(+)-glucosamine, and N-acetyl D-glucosamine. Other monosaccharides (e.g., 5-thio-glucose, D-galactose and D-fructose) and their derivatives can also be used. In addition, any of the monosaccharides and their derivatives described in PCT patent publication WO 01/82926, incorporated herein by reference, can be used to prepare a conjugate of the invention.

Some compounds are preferred for the conjugates used in the present methods. In other work, 6-[N-(7-nitrobenz-2-oxa-1,3-diazol-4-yl)amino]-6-deoxyglucose (6-NBDG) was used to study glucose uptake in certain cells. See, for example, Yoshioka et al., 1996, Biochimica et Biophysica Acta 1289: 5–9; Yamada et al., 21 Jul. 2000, J. Biol. Chem. 275(29): 22278–22283; Ball et al., 2002, Can. J. Physiol. Pharmacol. 80: 205–209; and Leira et al., 2002, Toxicology in Vitro 16: 267–273, each of which is incorporated herein by reference. This particular deoxyglucose conjugate is labeled with NBD at the 6-carbon position. The hydroxy group at the 6-carbon position is typically phosphorylated upon entry into a cell, inhibiting its diffusion from the cell. With conjugates carrying a fluorophore at this position, phosphorylation is less likely to occur, and the conjugate will thus be more likely to diffuse out of the cells. Conversely, fluorescent labeling of glucose or deoxyglucose at the 2-position or 3-position results in conjugates that can be phosphorylated after uptake by a cell, with the consequence that such conjugates are less likely to diffuse out of the cells. In addition, deoxyglucose derivatives are often preferred, as they are less likely to be hydrolyzed by esters and other enzymes in the cell. By accumulating the conjugate in the cells, sensitivity of the present method is increased; thus, conjugates of the present invention that have the fluorophore linked to the 2- or 3-position of the glucose, deoxyglucose or derivative are preferred.

Accordingly, in one embodiment, the fluorophore glucose, deoxyglucose or derivative conjugate of the present invention has a formula selected from:

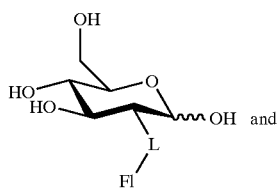

Ia and

-continued

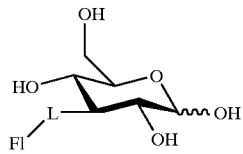

Ib wherein Fl and L have the meanings provided above.

Another preferred embodiment of the fluorophore glucose, deoxyglucose or derivative conjugate of the invention has the formula:

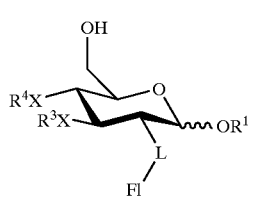

Ic wherein Fl is a fluorophore; L is a linking group; each X is independently selected from the group consisting of O and NH; and $R^1$, $R^3$ and $R^4$ are each members independently selected from the group consisting of H, $(C_1-C_{12})$alkyl, $(C_1-C_{12})$acyl and a solubility or partitioning effector component. The solubility or partitioning effector component is a component that increases the solubility of the resultant conjugate in aqueous solution relative to a conjugate having a hydrogen atom at the same position. Suitable solubility or partitioning effector components include oligoethylene glycol, oligopropylene glycol, polyhydroxylated carbon chains (typically two to thirty carbons in length) and the like.

In a preferred embodiment, the fluorophore glucose, deoxyglucose or derivative conjugate has the formula Ic in which each X is O, and $R^1$, $R^3$ and $R^4$ are each H.

In another preferred embodiment, the fluorophore glucose, deoxyglucose or derivative conjugate has the formula Ic in which each X is O, and two of $R^1$, $R^3$ and $R^4$ are H, with the remaining member of $R^1$, $R^3$ and $R^4$ being a solubility or partitioning effector component.

In a most preferred embodiment, L is attached to a glucose or deoxyglucose derivative by means of an amino or amido linkage (e.g., the glucose derivative is a 2-amino-2-deoxyglucose derivative).

Administering the Fluorophore Glucose or Deoxyglucose Conjugate

Administration of a fluorophore glucose or deoxyglucose conjugate provided herein can be effected by any method that enables delivery of the conjugates to the site of the cancer or suspected cancer. In one embodiment, delivery is via circulation in the bloodstream. To place the conjugates in contact with cancerous tissues or cells, the methods of administration include oral, buccal intraduodenal, parenteral injection (including intravenous, subcutaneous, intramuscular, intravascular, or infusion), topical administration, and rectal.

The amount of the conjugate administered will be dependent upon the subject being treated, the severity of the cancer, localization of the cancer, the rate of administration, the disposition of the conjugate (e.g., solubility and fluorescence intensity) and the discretion of the administrator. However, an effective dosage is typically in the range of about 0.001 to about 100 mg per kg body weight, preferably about 1 to about 35 mg/kg/day, in single or divided doses. For a 70 kg human, this dosage would amount to about 0.05 to about 7 g/day, preferably about 0.2 to about 2.5 g/day. In some instances, dosage levels below the lower limit of the aforesaid range may be more than adequate, while in other cases still larger doses may be employed without causing any harmful side effect, although such larger doses may be divided into several smaller doses for administration throughout the day.

The imaging fluorophore conjugate composition may, for example, be in a form suitable for oral administration, such as a tablet, capsule, pill, powder, sustained release formulation, solution, or suspension; for parenteral injection, such as a sterile solution, suspension or emulsion; for topical administration, such as an ointment or cream; or for rectal administration, such as a suppository. The imaging fluorophore conjugate composition may be in unit dosage forms suitable for single administration of precise dosages and can include a conventional pharmaceutical carrier or excipient.

Exemplary parenteral administration forms include solutions or suspensions of the imaging conjugate in sterile aqueous solutions, for example, aqueous propylene glycol or dextrose solutions. Such dosage forms can be suitably buffered, if desired.

Suitable pharmaceutical carriers include inert diluents or fillers, water, and various organic solvents. The pharmaceutical compositions may, if desired, contain additional ingredients such as flavorings, binders, excipients, and the like. Thus for oral administration, tablets containing various excipients, such as citric acid, may be employed together with various disintegrants such as starch, alginic acid, and certain complex silicates, and with binding agents such as sucrose, gelatin, and acacia. Additionally, lubricating agents such as magnesium stearate, sodium lauryl sulfate, and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the imaging fluorophore conjugate therein may be combined with various sweetening or flavoring agents, coloring matters or dyes, and, if desired, emulsifying agents or suspending agents, together with diluents such as water, ethanol, propylene glycol, glycerin, or combinations thereof.

Methods of preparing various pharmaceutical compositions with a specific amount of an active ingredient that are suitable for use with the active imaging fluorophore conjugates of the present invention are known, or will be apparent upon consideration of the disclosure herein, to those skilled in this art. For examples, see Remington's Pharmaceutical Sciences, Mack Publishing Company, Easter, Pa., 15th Edition (1975).

Because the imaging fluorescent conjugates of the present invention are preferentially taken up by cancer cells, it is possible to obtain an image of or visually confirm the presence of cancer cells that have taken up the conjugate. Detection of the conjugates can be performed using essentially any fluorescence detection device to obtain an image of the cancerous tissues or cells.

Detection of Cancer

Detection and imaging of tissues or cells that take up the conjugates described herein can be accomplished using visual techniques or via two-dimensional image information processing by direct continuous observation with a fluorescence microscope. While spatial resolution can be difficult for certain visual methods (unaided by spectral enhancers or microscopes), a typical fluorescence microscope can provide sufficient resolution at a single cell level.

For example, with a confocal laser scanning fluorescent microscope, 3-dimensional stereoscopic image information with a resolution of about 1 $\mu$m can be continuously obtained in real time from tissues in vivo. A variety of known methods can be adapted for use with the conjugates of the present invention. For example, the conjugates of the invention can be used in the endoscopic technique described in U.S. Pat. No. 5,261,410, in which an infrared monochromatic light source is employed and the Raman shift in emission radiation is measured to assess the tissue. Likewise, PCT patent publication No. WO 96/10363 discloses a method of normalization by dividing the intensity at each wavelength by the integrated area under the spectrum. Differences in the resulting curves are then used as the basis for diagnosis.

One of skill in the art will appreciate that essentially any fluorescence detection means, either microscopic or macroscopic, can be employed that is capable of detecting the fluorophore glucose or deoxyglucose conjugate localized in a particular lesion, tissue, organ, or cell.

In some embodiments, the detection means can be in the form of an endoscope inserted into a body cavity through an orifice, such as the mouth, nose, ear, anus, urethra, vagina or an incision. The term "endoscope" is used here to refer to any scope introduced into a body cavity, e.g., an anally introduced endoscope, an orally introduced bronchoscope, a urethrally introduced cystoscope, an abdominally introduced laparoscope, and the like. The miniaturization of scope components has greatly enhanced the utility of an endoscope, making endoscopes particularly useful in the practice of the present invention.

In addition to methods of detecting cancer as generally described above, certain embodiments of the present invention relate to intraoperative, laparoscopic, intravascular, and endoscopic examination, biopsy and treatment of tissues and/or organs with a fluorophore conjugate detecting means capable of close approach to suspected sites of tumor recurrence, metastasis, or incomplete removal of cancer tissue. As used herein, endoscopic procedures include laparoscopic procedures.

Embodiments of the present invention also relate to the intravascular, intraoperative, laparoscopic, and endoscopic examination of lesions with a fluorophore conjugate detecting means capable of close approach to suspected sites of the lesions, especially non-malignant pathological lesions. Lesions include cancerous, hyperplasic, and pre-cancerous cells or tissues.

As noted above, the methods of the present invention do not require processing of images. Rather, in one embodiment, a surgeon or clinician, through the use of, e.g., an intraoperative, laparoscopic, intravascular probe or an endoscope, can quickly scan areas of suspected tumor growth and use the level of fluorescence to more precisely discriminate tumor tissue from non-tumor tissue and thereby more precisely define tumor borders for surgical resection or diagnostic evaluation, or for laser or radiation therapy, including brachytherapy and external beam therapy, or for improved biopsy procedures.

Other embodiments enable the intravascular, intraoperative, laparoscopic, or endoscopic detection means to be similarly used to define and treat lesions. In another embodiment, the conjugate is useful for therapy of the detected tumor by emitting oxygen free radicals or other byproducts which damage the cells in which there has been accumulation of the conjugate. The emission of such damaging agents can be aided or induced by the energy which excites the fluorophore.

The above detection methods can be carried out in combination with a surgical procedure, such as a cancer resection. The method of detecting can be carried out endoscopically, for example, or visually as part of a skin examination for melanoma screening.

Methods of Detecting or Imaging Pre-Cancer

In a related aspect, the present invention provides methods for detecting pre-cancerous cells in a subject, comprising:

(a) administering to the subject an effective amount of a fluorophore glucose, deoxyglucose or derivative conjugate; and (b) detecting cells that take up the fluorophore glucose or deoxyglucose conjugate to determine if pre-cancerous cells are present in the subject.

The fluorophore conjugate used in this aspect of the invention is preferably one having the formula provided above as (I); more preferably having the formula provided above as (Ia) or (Ib); and most preferably one having the formula (Ic).

The application of the present method to detection and imaging of pre-cancerous cells (e.g., dysplastic cells) resides in the upregulated glucose transport that is exhibited by pre-cancerous cells. Generally, the conjugates, methods of administration and detection are the same as have been described above with respect to the detection and imaging of cancer cells.

Methods for Cancer or Pre-cancer Detection During an Operative or Endoscopic Procedure As noted above, the detection methods provided herein are broadly applicable and can be particularly effective when used in combination with surgical or endoscopic procedures.

Accordingly, in another related aspect, the present invention provides a method for cancer or pre-cancer detection during an operative or endoscopic procedure, the method comprising:

(a) administering to a patient subject to said procedure an effective amount of a fluorescent glucose, deoxyglucose or derivative conjugate, the conjugate having a rate of uptake in cancerous or pre-cancerous cells that is at least two times greater than the rate of uptake in normal cells;

(b) conducting the procedure within 48 hours of administering the conjugate; and (c) scanning the patient with a detection means for detecting the localization of the fluorescent conjugate in cancerous or pre-cancerous cells.

In this aspect, a fluorescent conjugate is administered to a patient prior to or coincident with a surgical procedure for the removal of cancerous tissue. The conjugate can be administered by any method designed to bring the conjugate into close proximity with the cancerous tissue, tumor, or lesion to be removed. In this manner, uptake of the conjugate by cancer cells will provide a more accurate determination of the cancer margins.

To facilitate detection during the operative or endoscopic procedure, the conjugate will typically be one that exhibits a rate of uptake in cancerous or pre-cancerous cells that is at least two times greater than the rate of uptake in normal cells (e.g., PBMC cells). Evaluation of such uptake can be carried out as described in the Examples below. Preferably, the rate of uptake in cancerous or pre-cancerous cells is at least 10 times the rate of uptake in normal cells, more preferably at least 20 times, and still more preferably at least 40 times.

For those embodiments in which the fluorescent conjugate is administered prior to the operative or endoscopic procedure, it will preferably be administered from about 1 hour to about 48 hours prior to the procedure, more preferably from about 1 hour to about 16 hours prior to the procedure, and most preferably from about 1 hour to about 6 hours prior to the procedure.

During the procedure, and depending upon the conjugate used, detection can be visual. In some embodiments, the fluorescence of cells that have taken up the conjugate can be enhanced by excitation of the fluorophore with light of a suitable wavelength. Accordingly, once a portion of the tumor or lesion is removed, the remaining tissue can be subjected to a suitable light source to excite the fluorescent conjugates that remain and additional resection can be accomplished.

In other embodiments, detection can be accomplished using fluoroscopes and other detection devices known to those of skill in the art.

Fluorophore Glucose, Deoxyglucose and Derivative Conjugates

In yet another aspect, the present invention provides fluorophore glucose, deoxyglucose and derivative conjugates having the formula:

Fl-L-Glc wherein Fl is a fluorophore having an emission wavelength of from about 400 nm to about 1200 nm; L is a bond or a linking group; and Glc is glucose, deoxyglucose or derivative, including deoxyglucose and derivatives thereof, with the proviso that the conjugate is other than 2-(N-(7-nitrobenz-2-oxa-1,3-diazol-4-yl)amino)-2-deoxyglucose.

As with the methods above, this aspect of the invention is directed to a variety of glucose, deoxyglucose and derivative conjugates. In particular, the fluorophores used in this aspect of the invention will typically be selected from coumarin dyes, nitrobenzoxazole dyes, cyanine dyes, dipyrrometheneboron dyes, xanthene dyes (including the benzo- and naphtho-xanthene dyes), phenoxazine dyes (as well as the benzo- and naphtho-phenoxazine dyes) and other classes well known to those of skill in the art. Illustrative embodiments of the fluorophore glucose or deoxyglucose conjugates of the invention and methods for their preparation are provided in the Examples below.

In one group of embodiments, L is a bond such that the fluorophore Fl is directly attached to Glc. Typically, this attachment is accomplished via coupling of a functional group on Fl with a compatible (e.g., linkage-forming) functional group on Glc. In certain preferred embodiments, Fl has an isocyanate, isothiocyanate or carboxylic acid functional group that is used to attach Fl to a hydroxy or amino group present on Glc to form a carbamate, thiocarbamate, urea or thiourea linkage between the components.

In another group of embodiments, L is a linking group which can be essentially any of the linking groups discussed above and generally known to those of skill in the art. The linking group in this aspect of the invention typically has from 3 to 100 main chain atoms other than hydrogen atoms, selected from C, N, O, S, P and Si, and can be cyclic, acyclic, aromatic or a combination thereof. Additionally, the linking groups are sufficiently robust so that they are stable not only to reaction conditions used in conjugate assembly, e.g., the protection/deprotection chemistries used to prepare the conjugates, but are also stable to conditions within a cancer cell.

More particularly, the linking group is one that is stable to hydrolytic and proteolytic conditions that are typically found in a cancer cell (e.g., exhibits a $t_{1/2}$ for hydrolysis or cleavage of the linkage of at least about 4 hours at ambient temperatures in a cancer cellular milieu). Preferred linking groups include both homo- and hetero-bifunctional linking groups, as are commercially available or readily prepared according to known methods.

The glucose or glucose derivative components of the conjugates described herein are preferably D-(+)-deoxyglucose, D-(+)-glucosamine and N-acetyl D-glucosamine. Other monosaccharides (e.g., D-galactose and D-fructose) can also be used.

In one group of preferred embodiments, the fluorophore glucose or deoxyglucose conjugate has a formula selected from:

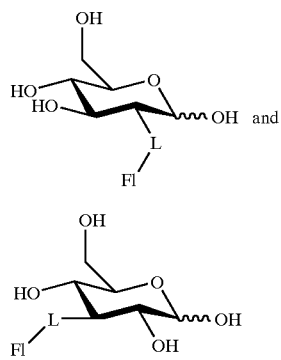

wherein Fl and L have the meanings provided above.

Still other preferred embodiments are those fluorophore glucose, deoxyglucose or derivative conjugates wherein the glucose portion is a 2-deoxy glucose, the conjugate having the formula:

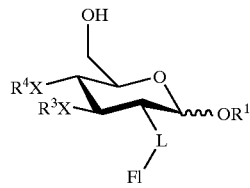

wherein Fl is a fluorophore; L is a linking group; each X is independently selected from the group consisting of O and NH; $R^1$, $R^3$ and $R^4$ are each members independently selected from the group consisting of H, $(C_1-C_{12})$alkyl, $(C_1-C_{12})$ acyl and a solubility or partitioning effector component. The solubility or partitioning effector component can be essentially any component that increases the solubility of the resultant conjugate in aqueous solution relative to the conjugate having a hydrogen atom at the same position. Suitable solubility or partitioning effector components include oligoethylene glycol, oligopropylene glycol, polyhydroxylated carbon chains (typically two to thirty carbons in length) and the like.

In a most preferred embodiment, the fluorophore conjugate has the formula Ic in which each X is O, and $R^1$, $R^3$ and $R^4$ are each H.

In another most preferred embodiment, the fluorophore conjugate has the formula Ic in which each X is O, and two of $R^1$, $R^3$ and $R^4$ are H, with the remaining member of $R^1$, $R^3$ and $R^4$ being a solubility or partitioning effector component.

In the most preferred embodiment, L is attached to the glucose framework by means of an amino or amido linkage (e.g., the deoxyglucose is a 2-amino-2-deoxyglucose).

Kits for Cancer Detection

In still another aspect, the present invention provides kits for use by a clinician, the kits having instructions for administration and cancer detection along with a sterile preparation of a fluorophore conjugate and a pharmaceutically acceptable carrier.

Other Applications

The fluorophore conjugates of the invention, while highly useful for the detection of cancer cells and tissues, can also be used in any application where a fluorescently labeled glucose, deoxyglucose or derivative molecule is useful. In one embodiment, the compounds of the invention are used to measure glucose uptake. In another embodiment, the compounds of the invention are used in an assay to determine whether a compound binds glucose or deoxyglucose. Likewise, while the methods and conjugates of the invention are especially valuable for the diagnosis and detection of cancer in humans, the methods and conjugates of the invention will also find application in the study and treatment of cancer in animals.

The following examples are offered by way of illustration and not by way of limitation.

EXAMPLE 1

This example illustrates the time course of uptake of 2-NBDG in Raji lymphoma cells.

Materials:

Raji cells from culture of one t-75 flask. Phosphate-buffered saline plus 2.5 mM $CaCl_2$, 1.2 mM $MgSO_4$, 4 mM KCl and 5 mM glucose (PBS+). 2-NBDG can be prepared in accordance with the method reported in Yoshioka et al., 1996, *Biochimica et Biophysica Acta* 1289: 5–9, incorporated herein by reference.

Uptake Reaction:

Culture medium with cells (15 mL) was centrifuged for 10 min at 800×g. The pellet of cells was resuspended in PBS+ and centrifuged for 10 min at 800×g, and the resulting pellet was resuspended in 1.5 mL PBS+. Aliquots (100 uL) were placed into each of 8 tubes and incubated at 37° C. for 15 min. The fluorophore deoxyglucose conjugate 2-NBDG was added to each tube to provide a concentration of 200 uM. A tube was removed from the 37° C. bath at each of 0, 1, 3, 5, 10, 20, 30 and 40 min and immediately placed on ice. The cells were washed twice with PBS and resuspended in 100 uL of PBS. A 20 uL aliquot was placed in each of 5 wells of an LJL 96-well plate and fluorescence was counted by a LJL plate reader. FIG. 1 shows the results of the time course experiment.

EXAMPLE 2

This example illustrates a comparison of 2-NBDG uptake in Raji lymphoma cells and peripheral blood white cells and illustrates the preferred uptake of a fluorophore deoxyglucose conjugate by a cancer cell as compared to a normal cell.

Materials:

Raji cells from culture one t-75 flask. Peripheral blood white cells from Stanford Blood Bank. Leukocytes were further separated by Ficoll separation (twice). These cells are referred to as PBMC (peripheral blood mononuclear cells). Phosphate-buffered saline. 2-NBDG, 0.1 M in water.

Figure 2A:
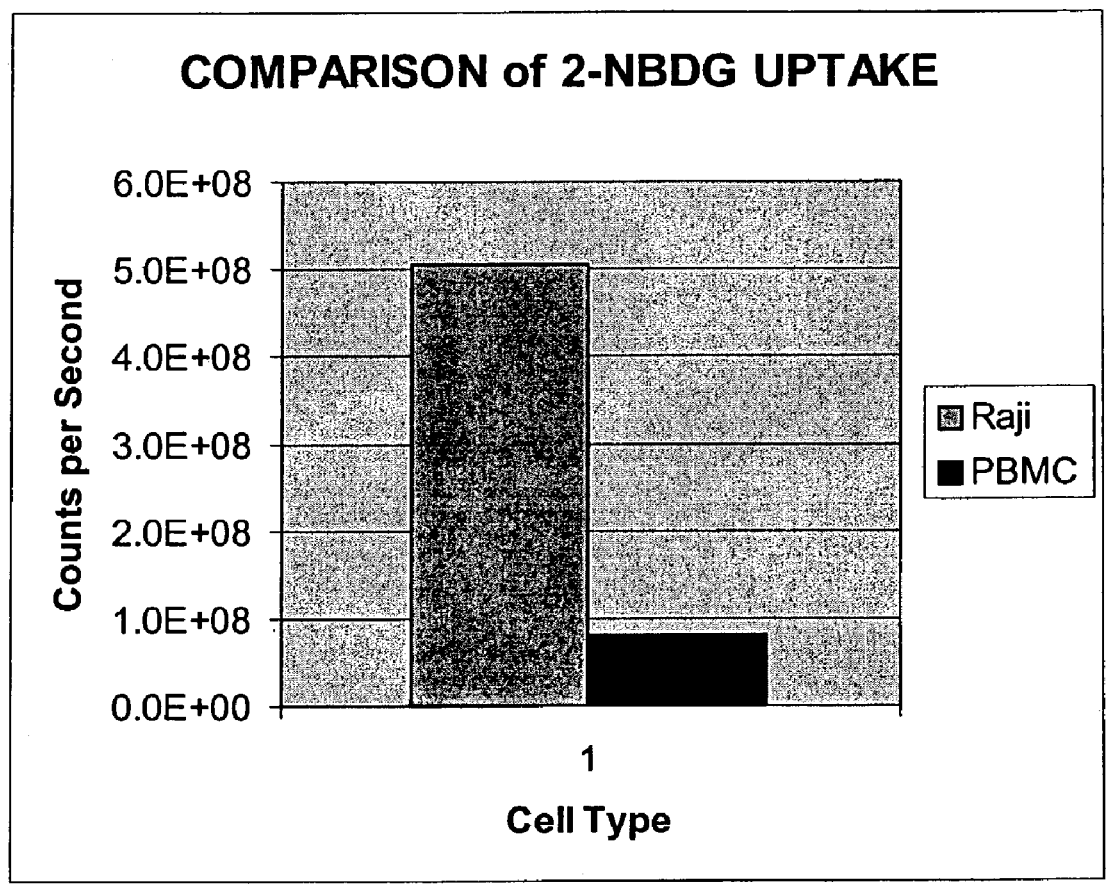
FIG. 2 is a histogram providing a comparison of 2-(N-(7-nitrobenz-2-oxa-1,3-diazol-4-yl)amino)-2-deoxyglucose uptake in Raji lymphoma cells versus non-cancer PBMC cells (FIG. 2A) and where the signals are normalized for the presence of red blood cells in PBMC (FIG. 2B).
Figure 2B:
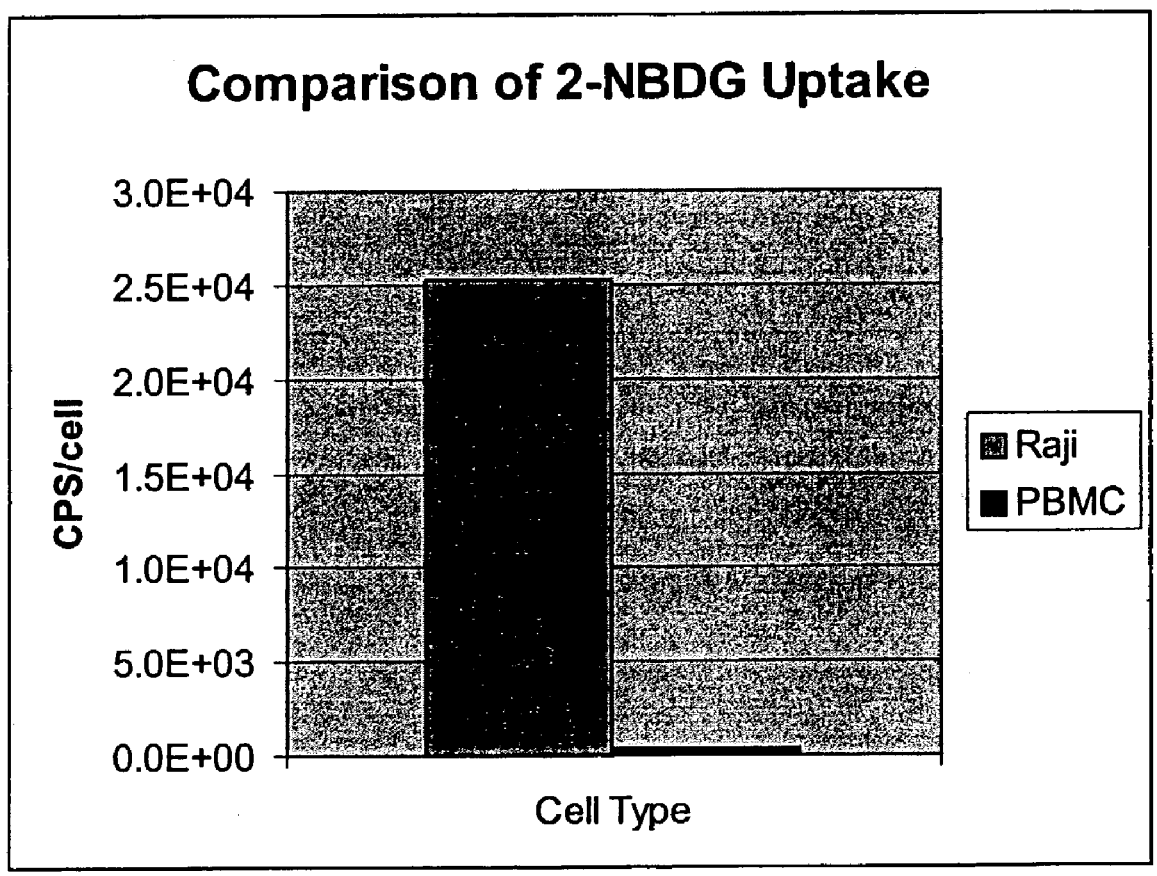

Uptake Reaction:

Culture medium with cells (either Raji or PBMC, 15 mL) were centrifuged for 10 min at 800×g. The pellet of cells was resuspended in PBS and centrifuged for 10 min at 800×g, and the resulting pellet was resuspended in 1.5 mL PBS. Cells were counted and adjusted to 1×10$^6$ per mL for both. Aliquots (100 uL) were placed into each of 2 tubes for each cell type, and the tubes were incubated at 37° C. for 15 min. The fluorescent deoxyglucose conjugate 2-NBDG was added to each tube to provide a concentration of 200 uM. At 40 min, the tubes were removed from the 37° C. bath and immediately placed on ice. The cells were washed twice with PBS and resuspended in 100 uL of PBS. A 20 uL aliquot was placed in each of 5 wells of an LJL 96-well plate, and fluorescence was counted by a LJL plate reader. FIG. 2 shows the results of the time course experiment.

EXAMPLE 3

This example illustrates the preparation of the fluorophore deoxyglucose conjugate of the invention FGC-002. In the conjugate, the fluorophore is BODIPY, and the glucose derivative is glucosamine.

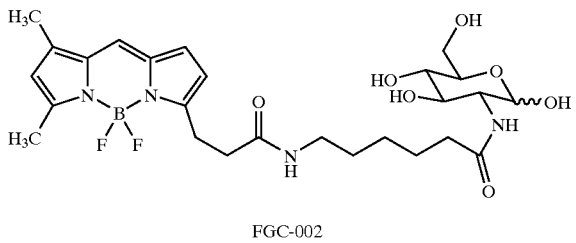

FGC-002

Generally, the FGC-002 conjugate is prepared by treating 6-((4,4-difluoro-5,7-dimethyl-4-bora-3a,4a-diaza-s-indacene-3-propionyl)amino)hexanoic acid, succinimidyl ester (BODIPY from Molecular Probes, D-2184, MW 502) with an excess of D-glucosamine (Sigma) in an aprotic solvent with gentle heating. Isolation of the product (FGC-002) can be accomplished via chromatography.

More particularly, 2.2 mg (4 micromoles) of 6-((4,4-difluoro-5,7-dimethyl-4-bora-3a,4a-diaza-s-indacene-3-propionyl)amino)hexanoic acid, succinimidyl ester was dissolved in 0.3 ml of DMF followed by the addition of 6 mg (28 micromoles) of glucosamine HCL dissolved in 0.3 ml of water and 3.9 microliters (28 micromoles) of triethyl amine. The reaction was stirred for 24 hrs at room temperature, evaporated under reduced pressure, and dissolved in a minimum of methanol. This solution was spread on a preparative TLC plate (silica), dried, and developed with 2.5% water in acetonitrile. The plate was then dried and the product visualized with a UV light. The only fluorescent band was scraped off the plate and then eluted with 10% water in acetonitrile and evaporated under reduced pressure, yielding 1 mg of product, which was soluble in methanol and sparingly soluble in water.

Figure 3:
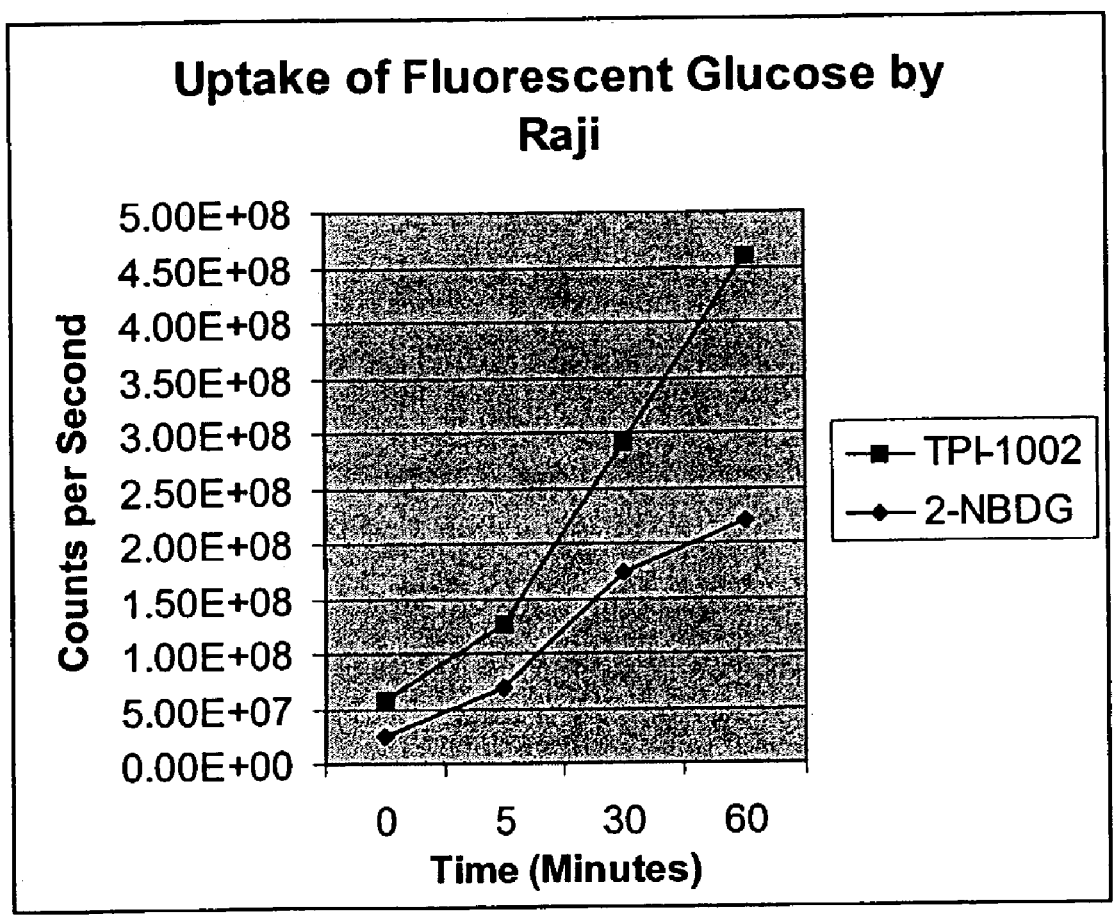
FIG. 3 is a graph illustrating the results of a time-course uptake of FGC-002 relative to 2-(N-(7-nitrobenz-2-oxa-1,3-diazol-4-yl)amino)-2-deoxyglucose in Raji lymphoma cells.

FIG. 3 illustrates a time-course uptake of FGC-002 relative to 2-(N-(7-nitrobenz-2-oxa-1,3-diazol-4-yl)amino)-2-deoxyglucose in Raji lymphoma cells. The uptake study was conducted substantially in accordance with the protocol described in Example 1.

EXAMPLE 4

This example provides synthetic methods for other illustrative fluorophore deoxyglucose conjugates of the invention.

A. Synthesis of Texas Red Glucosamine Conjugate

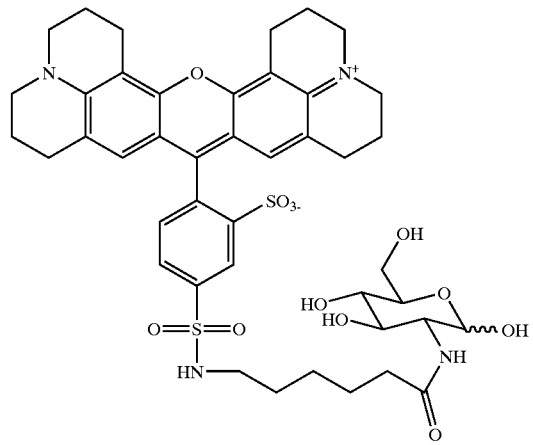

About 4 mg (4.8 micromoles) of Texas Red®-X, succinimidyl ester *single isomer* (816.94 MW, Molecular Probes, T-20175) were dissolved in 1.2 ml of methanol and combined with 4 mg (18 micromoles) of glucosamine HCl (Sigma) in 600 microliters of water. About 2.5 microliters (18 micromoles) of triethylamine were then added. The reaction was stirred overnight at 20° C. and then evaporated under reduced pressure. The gum was dissolved in methanol and spread on a preparative TLC plate (silica), dried, and developed with 10% water in acetonitrile. The plate was then dried and the product visualized with a UV light. The only red fluorescent band was scraped off the plate and then eluted with 20% water in acetonitrile and evaporated under reduced pressure, yielding 2 mgs of product which was soluble in methanol and sparingly soluble in water.

B. Synthesis of 5-(and 6) Carboxynaphtofluorescein Glucosamine Conjugate

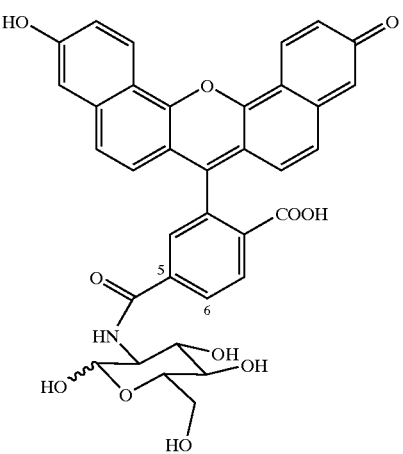

(5 isomer shown)

About 8.3 mg (14 micromoles) of 5-(and-6)-carboxynaphthofluorescein, succinimidyl ester *mixed isomers*

(MW 573.51, Molecular Probes, C-653) were dissolved in 2 ml of DMF, and 10 mg (46 micromoles) of glucosamine HCl (Sigma) in 1 ml of water was added. About 5.8 microliters (46 micromoles) of triethylamine were then added. The reaction was stirred overnight at 20° C. and then evaporated under reduced pressure. The gum was dissolved in 25% water in methanol and spread on a preparative TLC plate (silica), dried, and developed with 10% water in acetonitrile. The plate was then dried and the product visualized with a UV light. The only fluorescent band was scraped off the plate and then eluted with 20% water in acetonitrile and evaporated under reduced pressure, yielding 2 mgs of product, which was soluble in methanol and sparingly soluble in water.

C. Synthesis of Glucosamine N-Methylanthranilamide Conjugate

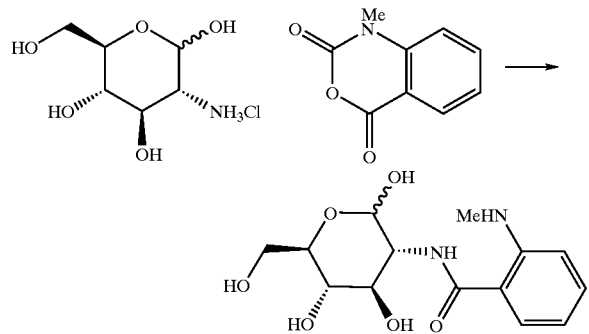

To a slurry of glucosamine (0.25 g, 1.2 mmol) and NEt$_3$ (1.0 mL, 7.0 mmol) in DMF (1 mL) was added a solution of N-methylitacoicanhydride (0.1 g, 0.56 mmol), and the resulting mixture was stirred at 80° C. for 18 h. The reaction mixture was filtered, adsorbed upon silica gel and separated on a silica gel column by washing with acetonitrile and eluting with 10% water in acetonitrile to yield 5 mg of the desired product.

EXAMPLE 5

This example illustrates the application of fluorophore conjugates of the present invention to procedures such as gastrointestinal colonoscopy.

Gastrointestinal Colonoscopy:

Endoscopic evaluation of the gastrointestinal tract is recommended for all individuals older than 50 years of age. This screening examination helps the physician identify polyps or other lesions which may be precancerous or cancerous but still localized in the intestine. Identification and removal of these lesions prevent spread of the disease and can cure most patients. This procedure suffers from some significant limitations, including difficulty in distinguishing between hyperplastic lesions and adenomatous lesions, the latter of which must be removed. With knowledge that a polyp is hyperplastic and not cancerous, the lesion can be ignored without removal and biopsy. In addition, some lesions are small and flat. These lesions are frequently overlooked and can be or become cancerous. Due to current limitations, some lesions are incompletely removed during the endoscopic procedure, which leads to an increased risk of recurrence.

To eliminate or ameliorate these limitations of endoscopy, fluorophore conjugates are administered to the patient by intravenous injection from 1 to 48 hours, preferably 2 to 6 hours, prior to the endoscopic procedure. The conjugate can be administered as an oral solution or by pill or as a suppository. The fluorophore conjugate circulates in the blood and accumulates in cancerous or precancerous tissue relative to normal or hyperplastic tissue. During endoscopy, the physician can view the colon under both white light and fluorescent capture. Specifically, while using white light, the physician sees a lesion that appears to be either hyperplastic or adenomatous. In particular, these lesions are viewed with fluorescent capture to determine if the lesion must be resected or can be ignored. Lesions that are highly fluorescent are clearly malignant or premalignant and are removed. Prior to completing this removal, the physician views the surrounding area by fluorescent capture to ensure that all of the malignant tissue is removed. In particular, the fluorophore conjugate can be used for patients who have conditions that put the patient at increased risk for the development of cancer. Patients who suffer this increased risk include patients with chronic inflammatory bowel disease and patients with Barrett's esophagus.

EXAMPLE 6

This example illustrates the utility of fluorophore conjugates of the present invention to tumor resection procedures.

Tumor Resection:

Patients diagnosed with a cancerous lesion can be cured if the lesion can be completely resected. Frequently, the surgeon takes tissue samples around the area of the resected tumor to examine the margins at the time of surgery. If the margins appear to contain cancer cells, the surgeon continues to remove tissue to complete the resection. This tissue examination helps the physician identify areas that may be precancerous or cancerous but not yet removed from the patient. Identification and removal of these lesions prevents spread of the disease and can cure the patient. This procedure suffers from some significant limitations, as it is time consuming, and samples from only a small area can be examined. Accordingly, many surgeons do not undertake this tissue sampling during the resection of the tumor but instead examine the tissue only after the surgery is completed. If malignant tissue has been left in the patient, further therapy, such as radiation therapy, is given to the patient. If the physician knew that malignant tissue remained in the patient at the time of surgery, a more complete resection could be effected, and an improved outcome for the patient would result.

To eliminate these limitations of surgical resection of cancer, fluorophore conjugates are administered to the patient by intravenous injection 1 to 48 hours, preferably 2 to 6 hours, prior to the tumor resection. The conjugate can alternatively be administered by oral solution or pill, circulates in the blood and accumulates in cancerous or precancerous tissue relative to normal tissue. During the surgery, the physician views the tissue under both white light and fluorescent capture. Specifically, the physician views an area that the physician has difficulty determining if it is normal or cancerous. In particular, the surgeon views the area of resected tissue prior to completing the operation to determine that all cancerous tissue has been removed. Areas remaining that emit fluorescence and therefore are clearly malignant or pre-malignant are removed. In particular, the fluorophore conjugate is used for patients who have cancers where such definitive removal is currently used. This includes removal of skin cancer by the Mohs' procedure that involves examination of successively collected sections of tissue to determine where the cancer remains and thus where to direct subsequent resection. The use of the fluorophore conjugate can improve the speed and ability of the surgeon to remove this type of cancer.

EXAMPLE 7

This example illustrates the utility of fluorophore glucose or deoxyglucose conjugates of the present invention in upper gastrointestinal endoscopy.

Upper Gastrointestinal Endoscopy:

Endoscopic evaluation of the upper gastrointestinal tract is recommended for many patients who have chronic gastroesophageal reflux and all individuals diagnosed with Barrett's esophagus. This screening examination helps the physician identify lesions that may be dysplastic, precancerous, or cancerous but still localized in the intestine. Identification and removal of these lesions prevents spread of the disease and can cure most patients. This procedure suffers from some significant limitations including difficulty in distinguishing between normal mucosa and dysplastic or precancerous lesions that must be removed. If the physician knew that there were areas of precancerous tissue, the patient would undergo surgical removal of the same and the lethal development of a cancer would be avoided. Due to current limitations, areas of precancerous tissue are often overlooked during endoscopy. Because the physician has no aid to find the areas of precancerous tissue, the physician must obtain biopsies in a random fashion, hoping to discover by chance the offending tissue if it exists.

To eliminate these limitations of endoscopy, a fluorescent conjugate of the invention is administered to the patient by intravenous injection 1 to 48 hours, preferably 2 to 6 hours, prior to the endoscopic procedure. This compound may alternatively be given by oral solution or pill. The conjugate circulates in the blood and accumulates in cancerous or precancerous tissue relative to normal tissue. During endoscopy, the physician views the esophagus under both white light and fluorescent capture. Specifically, using fluorescent capture, the physician can identify areas of increased fluorescence, which are deemed to be precancerous and which can be biopsied or removed as the physician deems appropriate.

All publications and patent applications cited in this specification are herein incorporated by reference as if each individual publication or patent application were specifically and individually incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for detecting or imaging cancer in a subject, said method comprising:
    (a) administering to said subject an effective amount of a dipyrromethene boron dye glucose or deoxyglucose conjugate; and
    (b) detecting or imaging cells that take up said conjugate to determine if cancer is present in said subject.

2. A method in accordance with claim 1, wherein said conjugate has the formula:

Fl-L-Glc wherein
Fl is a dipyrromethene boron dye;
L is a bond or a linking group; and
Glc is glucose or deoxyglucose.

3. A method in accordance with claim 2, wherein said Glc is deoxyglucose or a deoxyglucose derivative selected from the group consisting of D-(+)-deoxyglucose, D-(+)-glucosamine and N-acetyl D-glucosamine, and said Fl is a dipyrromethene boron dye having an emission wavelength of from about 400 nm to about 1200 nm.

4. A method in accordance with claim 2, wherein L is a linking group having from 2 to 30 chain atoms selected from the group consisting of C, N, O, P, S and Si.

5. A method in accordance with claim 2, wherein said conjugate has a formula selected from the group consisting of:

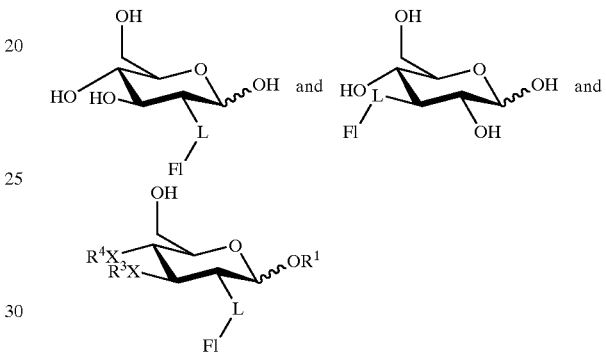

wherein
Fl is a dipyrromethene boron dye;
L is a linking group;
each X is independently selected from the group consisting of O and NH; and
$R^1$, $R^3$ and $R^4$ are each members independently selected from the group consisting of H, $(C_1-C_{12})$alkyl, $(C_1-C_{12})$acyl and a solubility or partitioning effector component selected from the group consisting of oligoethylene glycol, oligopropylene glycol, and a polyhydroxylated $(C_2-C_{30})$carbon chain.

6. A method in accordance with claim 1, wherein said detecting or imaging is carried out in combination with a cancer resection.

7. A method in accordance with claim 1, wherein said cancer cells are selected from the group consisting of lung cancer cells, breast cancer cells, prostate cancer cells, colon cancer cells, cervical cancer cells, esophageal cancer cells, bladder cancer cells, head and neck cancer cells and melanoma cells.

8. A method in accordance with claim 1, further comprising a preliminary step of reducing glucose ingestion in said subject.

9. A method of detecting pre-cancerous cells in a subject, said method comprising:
    (a) administering to said subject an effective amount of a dipyrromethene boron dye glucose or deoxyglucose conjugate; and
    (b) detecting or imaging pre-cancer cells that take up said conjugate to determine if pre-cancer cells are present in said subject.

10. A method in accordance with claim 9, wherein said conjugate has the formula:

Fl-L-Glc wherein

Fl is a dipyrromethene boron dye;

L is a bond or a linking group; and

Glc is glucose or deoxyglucose.

11. A method in accordance with claim 9, wherein said administering is intravenous, oral or topical.

12. A method in accordance with claim 11, wherein said pre-cancerous cells are associated with Barrett Esophagus, colonic polyps and inflammatory bowel disease.

13. A fluorophore conjugate having the formula:

Fl-L-Glc wherein

Fl is a dipyrromethene boron dye having an emission wavelength of from about 400 nm to about 1200 nm;

L is a bond or a linking group; and

Glc is glucose or deoxyglucose.

14. A fluorophore conjugate of claim 13, having a formula selected from the group consisting of:

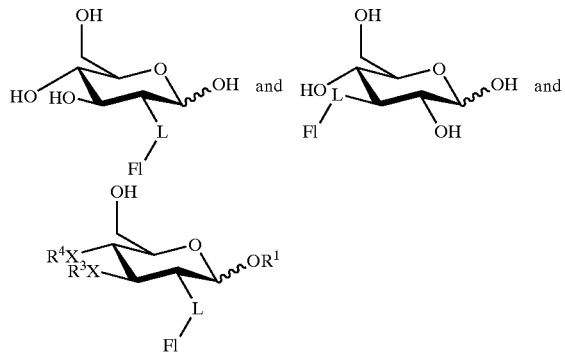

wherein

Fl is a dipyrromethene boron dye;

L is a linking group;

each X is independently selected from the group consisting of O and NH; and $R^1$, $R^3$ and $R^4$ are each members independently selected from the group consisting of H, $(C_1-C_{12})$alkyl, $(C_1-C_{12})$acyl and a solubility or partitioning effector component selected from the group consisting of oligoethylene glycol, oligopropylene glycol, and a polyhydroxylated $(C_2-C_{30})$carbon chain.

15. A method for cancer or pre-cancer detection during an operative or endoscopic procedure, said method comprising:

(a) administering to a patient subject to said procedure, an effective amount of a dipyrromethene boron dye glucose or deoxyglucose conjugate, said conjugate having a rate of uptake in cancerous or pre-cancerous cells that is at least two times greater than the rate of uptake in normal cells;

(b) conducting said procedure within 48 hours of said administering; and (c) scanning said patient with a detection means for detecting the localization of said conjugate in said cancer or pre-cancer cells, said detection means comprising a fluorescence microscope or a confocal laser scanning fluorescent microscope.

16. A method for cancer or pre-cancer detection in a patient undergoing an operative procedure or an endoscopic procedure, said method comprising:

(a) administering to said patient an effective amount of a dipyrromethene boron dye glucose or deoxyglucose conjugate, said conjugate having a rate of uptake in cancerous or pre-cancerous cells that is at least two times greater than the rate of uptake in normal cells;

(b) conducting said procedure within 24 hours after said administering step;

(c) scanning said patient with a detection means for detecting localization of said conjugate in said cancer or pre-cancer cells, said detection means comprising a fluorescence microscope or a confocal laser scanning fluorescent microscope; and (d) treating sites of conjugate accretion by external beam radiation, laser therapy, or surgical removal.

17. A kit comprising a vial containing a sterile preparation for human use of a dipyrromethene boron dye glucose or deoxyglucose conjugate and a pharmaceutically acceptable carrier.

* * * * *